(12) United States Patent
Rashan et al.

(10) Patent No.: US 7,569,237 B2
(45) Date of Patent: Aug. 4, 2009

(54) COMPOSITION FOR ENHANCING MALE FERTILITY

(75) Inventors: Luay Rashan, Amiria, Sult (JO); Fareed Rashan, Mosul (IQ); Abdullah-Abdelhalim Abo-Kadegha, Amman (JO); Ehab Rashan, Sult (JO); Raya Sahban, Amman (JO); Heinz-Herbert Fiebig, Freiburg (DE); Yahya Hamza Thanoon, Dubai (AE)

(73) Assignee: Luay Rashan, Amman, Shafa-Badran (JO)

( * ) Notice: Subject to any disclaimer, the term of this patent is extended or adjusted under 35 U.S.C. 154(b) by 0 days.

(21) Appl. No.: 11/853,661

(22) Filed: Sep. 11, 2007

(65) Prior Publication Data

US 2008/0113045 A1    May 15, 2008

(30) Foreign Application Priority Data

Sep. 15, 2006    (EP)    ................... 06019392

(51) Int. Cl.
    *A61K 36/23* (2006.01)
(52) U.S. Cl. ................ 424/756; 424/725; 424/776; 424/773
(58) Field of Classification Search ........ None
    See application file for complete search history.

(56) References Cited

U.S. PATENT DOCUMENTS

| 5,939,394 | A  | * | 8/1999  | Fleming et al. ........... 514/23 |
| 6,352,728 | B1 | * | 3/2002  | Butters et al. ........... 424/776 |
| 6,534,086 | B1 | * | 3/2003  | Krumhar .................. 424/464 |
| 6,884,442 | B2 | * | 4/2005  | Tani ....................... 424/745 |
| 2002/0061841 | A1 | * | 5/2002 | Nassief ..................... 514/7 |
| 2002/0132019 | A1 | * | 9/2002 | Kandil .................... 424/764 |
| 2003/0077336 | A1 | * | 4/2003 | Maffetone ............... 424/682 |
| 2004/0126441 | A1 | * | 7/2004 | Pushpangadan et al. ... 424/734 |

FOREIGN PATENT DOCUMENTS

| CN | 1583016 | * | 2/2005 |
| CN | 1814089 | * | 8/2006 |

OTHER PUBLICATIONS

Qureshi, et al., "Studies on Herbal Aphrodisiacs in Arab System of Medicine," American Journal of Chinese Medicine, vol. 17, No. 1-2, 1989, pp. 57-63.
European Search Report from corresponding European Application No. 060193292.7.
Abstract XP-002420172 of Chinese Patent CN1108564, 1995.
Abstract XP-002420173 of Chinese Patent CN1288743, 2001.

* cited by examiner

*Primary Examiner*—Susan C Hoffman
(74) *Attorney, Agent, or Firm*—Knobbe Martens Olson & Bear LLP

(57) ABSTRACT

The present invention relates to compositions for enhancing fertility in a male individual comprising extracts of radish seeds, celery seeds, black seeds and ginger rhizome, methods of enhancing fertility in a male individual comprising the step of administering said composition, and the use of said composition as a medicament.

17 Claims, No Drawings

COMPOSITION FOR ENHANCING MALE FERTILITY

FIELD OF THE INVENTION

The present invention relates to compositions for enhancing fertility in a male individual comprising extracts of radish seeds, celery seeds, black seeds and ginger rhizome, methods of enhancing fertility in a male individual comprising the step of administering said composition, and the use of said composition as a medicament.

BACKGROUND OF THE INVENTION

Approximately 15% of couples attempting their first pregnancy do not succeed. Most authorities define these individuals as infertile if they have been unable to achieve a pregnancy after one year of unprotected intercourse. Conception normally is achieved within twelve months in 80-85% of couples who use no contraceptive measures, and persons not conceiving after this time should therefore be regarded as possibly infertile and should be evaluated. Data available over the past twenty years reveal that in approximately 30% of cases pathology is found in the man alone, and in another 20% both the man and woman are abnormal. Therefore, the male factor is at least partly responsible in about 50% of infertile couples.

Sperm are produced by repeated division of cells in small coiled tubules within the testes at a rate of appropriately 100 million per day. Sperm production is a lengthy process, from the beginning of division of the stem cell to the appearance of mature sperm in the semen takes about 3 months. The sperm spend 2 to 10 days passing through the epididymis, during which time they mature and become capable of swimming and fertilising eggs. The volume of liquid from the testes and epididymides is less than 5% of the total semen volume. About 65% of the semen volume comes from the seminal vesicles and 25% from the prostate gland. The average semen volume for healthy men ejaculating every two days is 3 ml and the sperm concentration 85 million per ml. During ejaculation the sperm and the prostatic fluid come out first and the seminal vesicle fluid follows. The seminal vesicle fluid coagulates giving the semen a lumpy gel-like appearance. After 10 minutes or so liquefaction occurs and the gel disappears.

Male infertility may be caused by many conditions that affect the production of functional sperm. The most common cause is varicocele (i.e. hardening of the veins that drain the testes) which accounts for about 40% of cases and is treated surgically. Testicular failure accounts for approximately 10% of cases and may result from numerous causes including malignancy, mumps, Kleinfelter's syndrome, injury, and radio- or chemotherapy. Hyperspermia, increased seminal fluid volume, also accounts for about 10% of cases. Endocrine diseases affecting spermatogenesis account for approximately 9% of cases and usually involve pituitary or adrenal hypoplasia or hyperthyroidism. Obstruction of the ejaculatory duct accounts for about 5% of cases and sperm autoantibodies for 1 to 2%.

Approximately 13% of men have untreatable sterility, 11% have treatable conditions and 76% have disorders of sperm production or function which do not usually have clearly defined effective treatments. Of the 13% of men with untreatable sterility, most have no sperm in their semen (azoospermia) because the tubules in the testes which produce sperm did not develop or have been irreversibly damaged. This may be associated with failure of the testes to descend into the scrotum during childhood, inflammation of the testes or treatment with certain drugs. In some sterile men, sperm are produced in normal numbers, but they are either not motile (i.e. do not swim) or lack structures necessary for penetration and fertilisation of eggs which may be detected by microscope examination of the shape of the sperm and reported as abnormal morphology. Some men with failure of sperm production do not produce normal amounts of the male sex hormone, testosterone, and their general health and sexual performance is improved by treatment with testosterone. Over three quarters of men investigated for infertility have sperm present in the semen, but in lower numbers than normal—oligospermia (38%), or in adequate numbers but with reduced motility (33%).

Oligospermia is a condition associated with an abnormally low number of sperm in the ejaculate of the male. The normal range of sperm count is between 20 million/ml and 200 million/ml. The finding that the sperm count is below 20 million/ml indicates oligospermia. Common causes of oligospermia are stress, smoking of tobacco (nicotine damages sperms), lead (workers in printing press have low sperm count), hot climates, saunas, hot baths, the wearing of tight underwear, and other situations in which scrotal temperature may be raised, varicocele and consumption of alcohol.

SUMMARY OF THE INVENTION

Thus, the technical problem underlying the present invention is to provide new means/systems for enhancing/increasing male fertility.

The solution to the above technical problem is achieved by providing the embodiments characterized in the claims.

In particular, the present invention relates to a composition for enhancing fertility in a male individual comprising extracts of radish seeds, celery seeds, black seeds and ginger rhizome. It also relates to a method of enhancing fertility in a male individual comprising the step of administering said composition and a method of treating a male individual suffering from a disorder associated with reduced fertility comprising the step of administering said composition.

DETAILED DESCRIPTION OF THE PREFERRED EMBODIMENT

According to the present invention, the term "extract" means an aqueous extract. Said extract is obtainable by conventional methods known in the state of the art. Preferably, the extract is prepared by boiling a herbal mixture of radish seeds, celery seeds, black seeds and ginger rhizome (hereinafter simply referred to as "herbal mixture") in water for 1 to 8 minutes, cooling at room temperature and optionally filtrating the cooled mixture. It is more preferred to prepare the extract by boiling 2 to 5 parts by weight of herbal mixture in 100 parts by weight of water for 2 to 4 minutes, cooling for 10 to 15 minutes, and filtrating the cooled mixture to obtain the aqueous extract. Alternatively, it is possible to prepare the aqueous extracts of each herb separately and to combine the respective aqueous extracts to form the aqueous extract of the herbal mixture.

According to the present invention the term "radish" means wild radish (*Raphanus sativus*) of the family Brassicaceae. Radish contains volatile oils that are similar to those found in mustard. These include glucosinolates (mustard oil glycosides), gluconasturtiin, and sinigrin, which yield allyl isothiocyanate when broken down in the stomach.

Further, the term "celery" means *Apium graveolens* of the family Apicaceae and the term "celery seeds" refers to the fruits of said plant. Celery oil is dominated by terpenes, mostly limonene (70 to 80%) and the sesquiterpenes selinene (10%) and humulene, but its characteristic fragrance is caused by phthalides (3-butylphthalid and its 5,6-dihydro derivate sedanenolid), although the latter occur only in traces.

The term "black seeds" as used herein means the deep black, sharp-cornered seed grains of *Nigella sativa* of the family Ranunculaceae. The seeds contain numerous esters of structurally unusual unsaturated fatty acids with terpene alcohols (7%). Further, traces of alkaloids are found which belong to two different types: isochinoline alkaloids are represented by nigellimin and nigellimin-N-oxide, and pyrazol alkaloids include nigellidin and nigellicin. In the essential oil (avr. 0.5%, max. 1.5%), thymoquinone was identified as the main component (up to 50%) besides p-cymene (40%), pinene (up to 15%), dithymoquinone and thymohydroquinone. Other terpene derivatives were found only in trace amounts: Carvacrol, carvone, limonene, 4-terpineol, citronellol. Moreover, the essential oil contains significant (10%) amounts of fatty acid ethyl esters. On storage, thymoquinone yields dithymoquinonene and higher oligocondensation products (nigellone). The seeds also contain a fatty oil rich in unsaturated fatty acids, mainly linoleic acid (50 to 60%), oleic acid (20%), eicodadienoic acid (3%) and dihomolinoleic acid (10%) which is characteristic for the genus. Saturated fatty acids (palmitic, stearic acid) amount to about 30% or less.

Moreover, the term "ginger rhizome" refers to the large, fleshy rhizome of *Zingebare officinalis* of the family Zingiberaceae. The main constituents in ginger are phenolic compounds such as gingerols and shogaols, and sesquiterpenes such as zingiberene. These and other compounds are extracts found in ginger oleoresin. The main pungent flavor chemicals are the gingerols, which are not volatile.

In a preferred embodiment of the present invention, the composition for enhancing fertility in a male individual comprises 20 to 35 wt. % radish seeds extract, 20 to 35 wt. % celery seeds extract, 4 to 9 wt. % black seeds extract and 5 to 21 wt. % ginger rhizome extracts. Further, in a more preferred embodiment of the present invention, the composition for enhancing fertility in a male individual comprises 25 to 35 wt. % radish seeds extract, 25 to 35 wt. % celery seeds extract, 6 to 9 wt. % black seeds extract and 10 to 21 wt. % ginger rhizome extracts. Most preferably, the composition for enhancing fertility in a male individual consists of 35 wt. % radish seeds extract, 35 wt. % celery seeds extract, 9 wt. % black seeds extract and 21 wt. % ginger rhizome extracts.

Further, it should be noted that the term "individual" as used herein may be any mammal. In a preferred embodiment of the present invention the mammal is a breeding animal, like for example cats, dogs, cattle, horses, sheep, goats, pigs etc. In another preferred embodiment of the present invention, the individual is human.

In a preferred embodiment of the present invention the composition according to the present invention enhances the fertility of a male individual by increasing the number of spermatozoa, and/or enhancing the motility of spermatozoa, and/or adjusting the volume of the ejaculate and/or adjusting the liquefaction time of the ejaculate.

In a preferred embodiment the composition according to the present invention further comprises vitamin E in a therapeutically effective amount, preferably in an amount of 6 to 20 wt. %, more preferred in an amount of 8 to 12 wt. %, with respect to the total weight of the extracts. Preferably, the daily dose of Vitamin E should be in the range of about 400 to about 800 IU. Vitamin E has been found to further enhance the sperm motility.

Suitable methods for the determination of the increase of the number of spermatozoa, the enhancement of the motility of spermatozoa, the adjustment of the volume of the ejaculate and the adjustment of the liquefaction time of the ejaculate are known to those skilled in the art.

The present invention further relates to a method of enhancing fertility in a male individual comprising the step of administering the composition according to the present invention. In a preferred embodiment of the present invention, the composition is administered orally.

The composition according to the present invention is preferably administered in the form of an aqueous extract obtained from 1 to 5 g, more preferable from about 3 g of herbal mixture. In a preferred embodiment of the present invention the extract of the present invention is diluted 1 to 5 times before administration. In another preferred embodiment, the extract according to the present invention is further processed into capsules or tablets and is administered in one of said dosage forms. Suited methods for preparing capsules or tables from an aqueous extract are known in the state of the art.

Moreover, a method of treating a male individual suffering from a disorder associated with reduced fertility comprising the step of administering the composition according to the present invention is provided. In a preferred embodiment of the present invention, said disorder is associated with a reduced number of spermatozoa, and/or reduced motility of spermatozoa, and/or reduced volume of the ejaculate, and/or reduced liquefaction time of the ejaculate. In an especially preferred embodiment of the present invention said disorder is oligospermia. In another especially preferred embodiment of the present invention said disorder is varicose testes leading to male infertility.

In a preferred embodiment of the method of treating a male individual suffering from a disorder associated with reduced fertility, the composition according to the present invention is administered once a day for a time period of at least 70 days, more preferably for at least 80 days. However, it is noted that in dependence on the single case, the composition of the present invention may be administered for a time period of 6 to 18 months. In a further preferred embodiment of the method of treating a male individual suffering from a disorder associated with reduced fertility, the composition is administered after dinner.

In another preferred embodiment of the method of treating a male individual suffering from a disorder associated with reduced fertility, the fertility is enhanced for at least 60%, more preferably for at least 65% and most preferably for at least 75% after treatment with the composition according to the present invention. When using the method of treating a male individual suffering from a disorder associated with reduced fertility according to the present invention, the enhancement of fertility depends on the initial sperm count before the beginning of the treatment, i.e. a higher enhancement can generally be obtained, when the initial sperm count before beginning of the treatment is low.

Additionally, the present invention relates to the use of the composition according to the present invention as a medicament. In this context, the medicament may optionally contain one or more pharmaceutically acceptable carriers and/or diluents and/or auxiliary agents.

Moreover, the present invention relates to the use of the composition according to the present invention in the manufacture of a medicament for treating a male individual suffering from a disorder associated with reduced fertility. In a preferred embodiment of the present invention said disorder is associated with a reduced number of spermatozoa, and/or reduced motility of spermatozoa, and/or reduced volume of the ejaculate and/or reduced liquefaction time of the ejaculate. In an especially preferred embodiment of the present invention said disorder is oligospermia. In another especially preferred embodiment of the present invention said disorder is varicose testes leading to male infertility.

EXAMPLES

Example 1

Preparation of Plant Extracts

The plant extracts have been prepared by boiling 3 g of each of the desired herbs, such as radish seeds, celery seeds, black seeds and ginger rhizome, in 100 ml of water for 3 minutes, cooling the resulting mixture at room temperature for 10 to 15 minutes and filtrating off the solid components.

Example 2

Preparation of a Preferred Embodiment of the Composition According to the Present Invention (Fertilin)

The plant extracts of Example 1 have been mixed so that a preferred embodiment of the composition according to the present invention (Fertilin) consisting of 35 wt. % radish seeds extract, 35 wt. % celery seeds extract, 9 wt. % black seeds extract and 21 wt. % ginger rhizome extracts has been obtained. After that 3 g of said composition have been boiled in 100 ml of water for about three minutes, cooled at room temperature for 10 to 15 minutes and filtered.

Example 3

Method of Treatment

The composition prepared according to Example 2 has been administered orally to a group of individuals suffering from a disorder associated with a reduced number of spermatozoa, reduced motility of spermatozoa, reduced volume of the ejaculate and/or reduced liquefaction time of the ejaculate once a night after dinner continuously for a period of 70 to 80 days depending on the number of spermatozoa, followed by 5 days of abstinence. Then, a laboratory semen analysis has been carried out. The results have been compared with the respective semen analysis carried out prior to the treatment.

The results for the tested group of individuals are summarized in the following Table 1.

TABLE 1

| Type of infertility | Number of individuals | Response [%] |
| --- | --- | --- |
| Primary infertility | 95 | 76 |
| Secondary infertility | 83 | 65 |
| Severe oligospermia | 210 | 50 |
| Moderate oligospermia | 18 | 82 |

The results obtained from the above study show that the use of the composition according to the present invention for treating male individuals suffering from a disorder associated with reduced fertility, leads to the remarkable effect of increasing the number of spermatozoa (50 to 82%) in cases ranging from severe oligospermia (defined as an oligospermia with an initial sperm count of less than 1,000,000/ml) to cases of moderate oligospermia (defined as an oligospermia with an initial sperm count of less than 20,000,000/ml).

Further, the effect of the composition according to the present invention on the viscosity (i.e. the liquefaction time) has been evaluated. The respective results are shown in the following Table 2.

TABLE 2

| Number of individuals before treatment | Viscosity before treatment [hrs] | Number of individuals recovered after treatment | Viscosity after treatment [minutes] |
| --- | --- | --- | --- |
| 520 | 3 to 24 | 412 | 20 to 30 |

The above results clearly show that the treatment of male individuals suffering from a disorder associated with reduced fertility using the composition according to the present invention, has a positive effect on the viscosity of the spermatozoa in more than 80% of the treated cases.

The time required for this treatment to adjust the liquefaction time varies. However, a minimum period of 75 days is required.

Further, the effect of the composition according to the present invention on the sperm motility has been evaluated. The respective results are shown in the following Table 3.

TABLE 3

| Number of individuals | Sperm motility before treatment [% in 30 min] | Sperm motility after treatment [% in 30 min] |
| --- | --- | --- |
| 320 | 10 | 22 |

The above results clearly show that the treatment of male individuals suffering from a disorder associated with reduced fertility using the composition according to the present invention, has also a positive effect on the sperm motility.

In summary, the above results clearly indicate that the treatment of male individuals suffering from a disorder associated with reduced fertility using the composition according to the present invention leads to an increased number of spermatozoa, improves the viscosity of the spermatozoa and improves the sperm motility, thus significantly improving the male fertility.

What is claimed is:

1. A composition for enhancing fertility in a male individual comprising 20 to 35 wt. % aqueous extracts of radish seeds, 20 to 35 wt. % aqueous celery seeds extract, 4 to 9 wt. % aqueous black seeds extract and 5 to 21 wt. % aqueous ginger rhizome extract.

2. The composition according to claim 1, comprising 25 to 35 wt. % radish seeds extract, 25 to 35 wt. % celery seeds extract, 6 to 9 wt. % black seeds extract and 10 to 21 wt. % ginger rhizome extracts.

3. The composition according to claim 1, consisting of 35% radish seeds extract, 35% celery seeds extract, 9% black seeds extract, and 21% ginger rhizome extracts.

4. The composition according to claim 1, wherein the individual is human.

5. The composition according to claim 1, wherein the fertility is enhanced by increasing the number of spermatozoa, and/or enhancing the motility of spermatozoa, and/or adjusting the volume of the ejaculate, and/or adjusting the liquefaction time of the ejaculate.

6. The composition according to claim 1, further comprising vitamin B in a therapeutically effective amount.

7. A method of enhancing fertility in a male individual comprising the step of administering the composition according to claim 1 to said individual.

8. The method according to claim 7, wherein the composition comprises 25 to 35 wt. % radish seeds extract, 25 to 35 wt. % celery seeds extract, 6 to 9 wt. % black seeds extract and 10 to 21 wt. % ginger rhizome extracts.

9. The method according to claim 7, wherein the composition consists of 35% radish seeds extract, 35% celery seeds extract, 9% black seeds extract, and 21% ginger rhizome extracts.

10. A method of treating a male individual suffering from reduced fertility comprising the step of administering the composition according to claim 1.

11. The method according to claim 10, wherein the reduced fertility is associated with a reduced number of spermatozoa, and/or reduced motility of spermatozoa, and/or reduced volume of the ejaculate, and/or reduced liquefaction time of the ejaculate.

12. The method according to claim 11, wherein the reduced fertility is due to oligospermia.

13. The method according to claim 10, wherein the fertility is enhanced for at least 60% of individuals receiving treatment.

14. The method according to claim 10, wherein the fertility is enhanced for at least 65% of individuals receiving treatment.

15. The method according to claim 10, wherein the fertility is enhanced for at least 75% of individuals receiving treatment.

16. The method according to claim 10, wherein the composition comprises 25 to 35 wt. % radish seeds extract, 25 to 35 wt. % celery seeds extract, 6 to 9 wt. % black seeds extract and 10 to 21 wt. % ginger rhizome extracts.

17. The method according to claim 10, wherein the composition consists of 35% radish seeds extract, 35% celery seeds extract, 9% black seeds extract, and 21% ginger rhizome extracts.

* * * * *